United States Patent [19]

Yevich et al.

[11] Patent Number: 4,668,687
[45] Date of Patent: May 26, 1987

[54] PSYCHOGERIATRIC 1-(2-PYRIMIDINYL)PIPERAZINYL DERIVATIVES OF 1-PYRROLIDIN-2-ONES

[75] Inventors: Joseph P. Yevich, Newburgh; Ronald J. Mattson, Evansville, both of Ind.

[73] Assignee: Bristol-Myers Company, New York, N.Y.

[21] Appl. No.: 799,670

[22] Filed: Nov. 19, 1985

Related U.S. Application Data

[63] Continuation-in-part of Ser. No. 633,371, Jul. 23, 1984.

[51] Int. Cl.$^4$ .................. A61K 31/505; C07D 403/04
[52] U.S. Cl. .................................. 514/252; 544/295; 544/372
[58] Field of Search ........................ 544/295; 514/252

[56] References Cited

U.S. PATENT DOCUMENTS

| | | | |
|---|---|---|---|
| 3,717,634 | 2/1973 | Wu et al. | 544/395 |
| 4,145,347 | 3/1979 | L'Italien et al. | 544/372 |
| 4,216,216 | 8/1980 | Weber et al. | 544/295 |
| 4,372,960 | 2/1983 | L'Italien et al. | 544/372 |
| 4,420,481 | 12/1983 | Okazaki et al. | 544/372 |
| 4,423,049 | 12/1983 | Temple | 544/231 |
| 4,524,206 | 7/1985 | New et al. | 544/295 |
| 4,605,655 | 8/1986 | Yeyich et al. | 544/295 |

FOREIGN PATENT DOCUMENTS

0089900 9/1983 European Pat. Off. .
2023594 1/1980 United Kingdom .

OTHER PUBLICATIONS

Malawska, et al., "Synthesis and Pharmacological Properties of Some 2-Pyrrolidinone Mannich Bases", Polish Journal of Pharmacology, 1982, 34, 373–382.

*Primary Examiner*—Glennon H. Hollrah
*Assistant Examiner*—James H. Turnipseed
*Attorney, Agent, or Firm*—Richard P. Ryan; Robert E. Carnahan

[57] ABSTRACT

A series of nootropic compounds of the following formula:

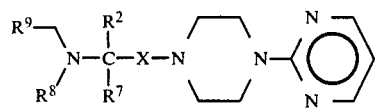

and its pharmaceutically acceptable acid addition salts, wherein:

$R^2$ is hydrogen, lower alkyl, aryl which is optimally substituted, or hetaryl;

$R^7$ is hydrogen or is combined with $R^9$ as a fused benzo-ring;

$R^8$ is hydrogen or lower alkyl; and $R^9$ is lower alkyl, or $R^9$ can be combined with $R^8$ to give a 2-pyrrolidinone, a phthalimide, or isoindolone ring system.

Pharmacological testing demonstrates that the series possesses cognition and memory enhancing actions and/or mild CNS simulation.

24 Claims, No Drawings

PSYCHOGERIATRIC 1-(2-PYRIMIDINYL)PIPERAZINYL DERIVATIVES OF 1-PYRROLIDIN-2-ONES

CROSS-REFERENCE TO RELATED APPLICATION

This is a continuation-in-part application of Ser. No. 633,371 filed July 23, 1984 and now abandoned.

BACKGROUND OF THE INVENTION

This invention generally pertains to heterocyclic carbon compounds having drug and bio-affecting properties and to their preparation and use. In particular, the invention is concerned with 1,4-disubstituted piperazine derivatives wherein one substituent is a pyrimidin-2-yl ring and the other is a 1-pyrrolidin-2-one ring linked by a bridging moiety to the piperazine nitrogen atom. The compounds of this invention are applicable in the treatment of various senile dementias affecting adults.

The clinical aspects of various senile dementias as well as the problems they cause in the affected adult subject are well known to those skilled in the art. One will also appreciate that various drug treatments of this disorder are currently under study. Among such drugs are a class of drugs known as nootropic agents or, more commonly, cognition enhancers; some of which are currently undergoing clinical evaluation in patients diagnosed as having Alzheimer's disease, a serious and fairly common CNS disorder. Chemically, these drugs under clinical study are members of a class of N-substituted 2-pyrrolidinone derivatives of structure 1.

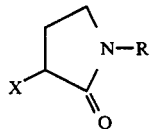

a: X=H; R=—CH$_2$CONH$_2$ (piraacetam)
b: X=OH; R=—CH$_2$CONH$_2$ (oxiracetam)
c: X=H; R=—CH$_2$CONH[CH$_2$]$_2$N[CH(CH$_3$)$_2$]$_2$ (pramiracetam)
d: X=H;

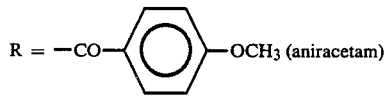

Preliminary clinical results with this class of agents, exemplified by structures 1a–d, indicates that these drugs may have some beneficial effects in treating senile dementias.

Related art may be viewed in light of the following general structural formula 2

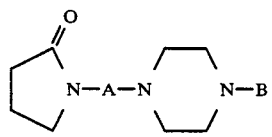

in which A is a bridging moiety such as alkyl, alkanoyl, alkylamidoalkyl, and the like; and B is a substituent group.

In Great Britain No. 2,023,594, a series of 1-substituted alkyl-4-(3-trifluoromethylthiophenyl)-piperazines were disclosed as being useful in treatment of anxiety and depression. Specifically disclosed were compounds of structurre 3.

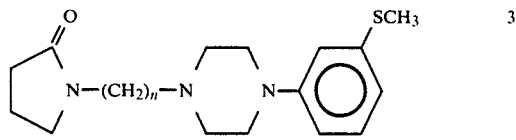

wherein n=2, 3.

U.S. Pat. No. 4,145,347, issued Mar. 20, 1979 to L'Italien, et al. disclosed a series of N-(substituted-aminoalkyl)-2-oxo-1-pyrrolidine acid amides as cognition activators potentially useful in treating patients suffering from senility. The most relevant compounds disclosed in this patent have structural formula 4.

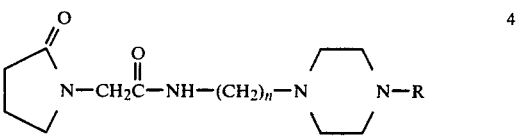

wherein:
n=1–4
R=C$_{1-4}$ alkyl, specifically methyl.

A second patent, U.S. Pat. No. 4,372,960, issued Feb. 8, 1983 to L'Italien disclosed a series of quaternary derivatives of N-(substituted-aminoalkyl)-2-oxo-1-pyrrolidine acid amides. These compounds of structural formula 5 are disclosed as being useful in the treatment of senility, memory enhancement and amnesia reversal.

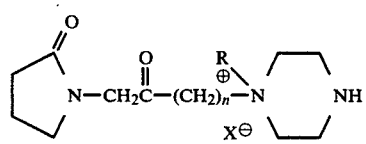

wherein:
n=1–4
R=C$_{1-3}$ alkyl
X$^\ominus$=a pharmaceutically acceptable anion.

European Patent Application No. 89,900, published Sept. 28, 1983 concerns a series of piperazine derivatives of formula 6 which are disclosed as drugs especially useful in the treatment of cerebral vascular disturbances in the elderly.

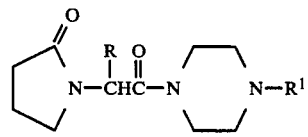

wherein:
R is hydrogen or C$_{1-3}$ alkyl; and
R$^1$ is an allyl, cinnamyl or p-methoxybenzyl group.

Malawska, et al., "Synthesis and Pharmacological Properties of Some 2-Pyrrolidinone Mannich Bases" in Polish Journal of Pharmacology, 1982, 34, 373–382, disclose a series of compounds of which one subclass is represented by structural formula 7. These compounds reportedly displayed analgesic properties as well as weak anti-inflammatory action.

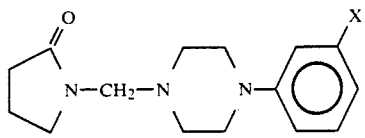   7 wherein X is hydrogen or chlorine.

All of the above referenced compounds differ from the series of compounds of the instant invention in which B is a 2-pyrimidinyl heterocyclic ring as compared with the reference compounds wherein B is alkyl, aryl, or aralkyl. The following reference compounds are even less related than the foregoing.

A large number of psychotropic compounds with structures corresponding to formula 8 have been disclosed by Wu, Temple, New, and co-workers.

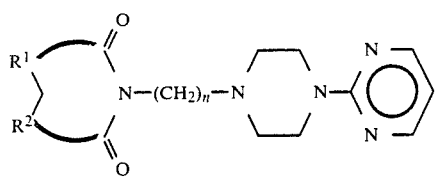   8 wherein n is from 2 to 6.

These compounds of structure 8 and similar analogs, however, are N-substituted cyclic imide rings, e.g. succinimides, glutarimides, etc. and easily distinguished from the compounds of the instant invention.

See:
Wu, et al., U.S. Pat. No. 3,717,634 patented Feb. 20, 1973. Temple, U.S. Pat. No. 4,423,049 patented Dec. 27, 1983. New and Yevich, pending application Ser. No. 531,519, filed Sept. 12, 1983.

Similarly, the compounds disclosed by Okazaki, et al., in U.S. Pat. No. 4,420,481 issued Dec. 13, 1983, (cf: structural formula 9); and Weber, et al. in U.S. Pat. No. 4,216,216, issued Aug. 5, 1980, (cf: structural formula 10);

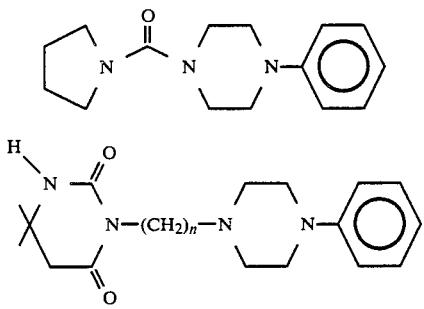

can be distinguished from the compounds of the instant invention by virtue of these structures lacking both a lactam ring as well as a 2-pyrimidinyl ring moiety.

In summary, there are no teachings in the art which would make the specific compounds comprising the instant invention anticipated or obvious.

SUMMARY OF THE INVENTION

A series of compounds of structural Formula I

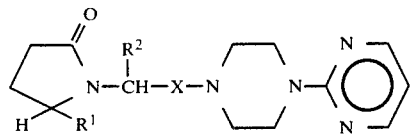   I wherein
$R^1$ is hydrogen or lower alkyl;
$R^2$ is hydrogen, lower alkyl, unsubstituted aryl or aryl optimally substituted at one or more ring positions with lower alkyl, halogen, $-CF_3$, $-CN$, $-NO_2$,

$-NR^3_2$, $-CO_2R^4$, or $OR^5$, with $R^3$ being H or lower alkyl, $R^4$ being $R^3$, phenyl or phenalkyl, and $R^5$ being $R^4$; and
X is a chemical bond,

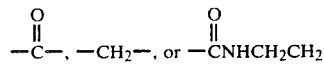

has been prepared. Compounds of this series can be incorporated into pharmaceutical compositions for use in adult subjects afflicted with senile dementias. A number of these compounds have been tested and display cognition enhancing action and/or mild CNS stimulation. These actions have been demonstrated by EEG and prevention of ECS-induced amnesia in rats and maze-testing of aged rats.

DETAILED DESCRIPTION OF THE INVENTION

In its broadest aspect, the present invention is concerned with 1-(2-pyrimidinyl)piperazinyl 1-pyrrolidin-2-one derivatives having psychogeriatric properties and characterized by structural Formula I

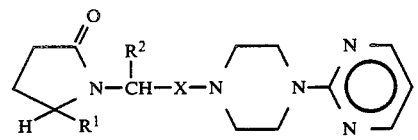   I wherein
$R^1$ is hydrogen or lower alkyl;
$R^2$ is hydrogen, lower alkyl, unsubstituted aryl or aryl optimally substituted at one or more ring positions with lower alkyl, halogen, $-CF_3$, $-CN$, $-NO_2$,

$-NR^3_2$, $-CO_2R^4$, or $OR^5$, with $R^3$ being H or lower alkyl, $R^4$ being $R^3$, phenyl or phenalkyl, and $R^5$ being $R^4$;
X is a chemical bond,

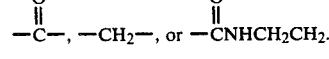

By lower alkyl is meant that these groupings contain from one to four carbon atoms. Halogen means F, Cl, Br, or I and aryl means phenyl or naphthyl. For preferred compounds, $R^1$ and $R^2$ are hydrogen, and for the most preferred compound, X is a chemical bond.

It is to be understood that the present invention is considered to include the various stereoisomers, e.g. optical isomers including individual enantiomers, mixtures of enantiomers, diastereomers, and mixtures of diastereomers, which can arise as a consequence of structural asymmetry due to the presence of one or two asymmetric carbon atoms which may be incorporated into some compounds of the instant series. Separation of the individual isomers is accomplished by application of various methods which are well known to practitioners in the art.

For medicinal use, the pharmaceutically acceptable acid addition salts, those salts in which the anion does not contribute significantly to toxicity or pharmacological activity of the organic cation, may be preferred in some cases. The acid addition salts are obtained either by reaction of an organic base of structure I with an organic or inorganic acid, preferably by contact in solution, or by any of the standard methods detailed in the literature available to any practitioner skilled in the art. Examples of useful organic acids are carboxylic acids such as maleic acid, acetic acid, tartaric acid, propionic acid, fumaric acid, isethionic acid, succinic acid, pamoic acid, cyclamic acid, pivalic acid, and the like; useful inorganic acids are hydrohalide acids such as HCl, HBr, HI; sulfuric acid; phosphoric acid; and the like.

The compounds of the instant invention can be prepared via several synthetic methods which are modifications of a unitary process which is shown in Scheme 1.

Scheme 1
Unitary Process

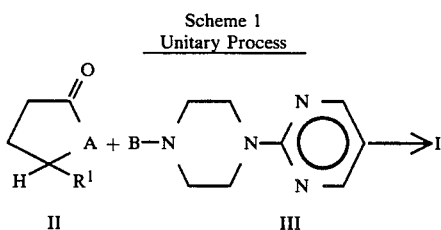

In this scheme, $R^1$ and $R^2$ will have the same meanings as previously assigned to them in Formula I. The symbol "A" can be >NH; >O; or >N—CH$_2$CO$_2$Me. The symbol "B" can be H—; [R$^2$HC=]; or H$_2$NCHR$^2$—X—. The relationship between A and B is:

| Method No. | A | B | C |
|---|---|---|---|
| When A is: | NH (IIa) | O (IIb) | NCH$_2$CO$_2$Me (IIc) |
| then B is: | [R$^2$HC =] (IIIa) | H$_2$NCHR$^2$CH$_2$— (IIIb) | H (IIIc) or H$_2$NCHR$^2$CH$_2$ (IIIb) |

The grouping [R$^2$HC=] (IIIa) represents the intermediate reaction complex formed between IIIc B=H; and R$^2$CHO. This transient reaction intermediate undergoes rapid attack by IIa, A=NH; to give I.

Accordingly, the process of the instant invention for preparation of compounds of Formula I

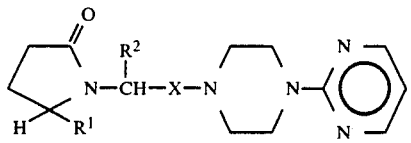

wherein $R^1$, $R^2$, and X are as previously defined comprises the condensation of a compound of Formula II

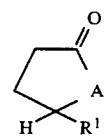

wherein A is >NH, >O, or >NCH$_2$CO$_2$Me; with a compound of Formula III

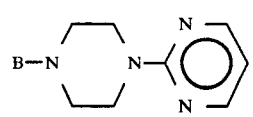

wherein B is [R$^2$HC=], H$_2$NCHR$^2$CH$_2$, or H; with the proviso that when A is NH, B is [R$^2$HC=]; when A is O, B is H$_2$NCHR$^2$CH$_2$—; and when A is NCH$_2$CO$_2$Me, B is H or H$_2$NCHR$^2$CH$_2$.

These methods comprising the unitary process are more fully illustrated by the reaction schemes shown in Scheme 2.

Scheme 2

Method A:

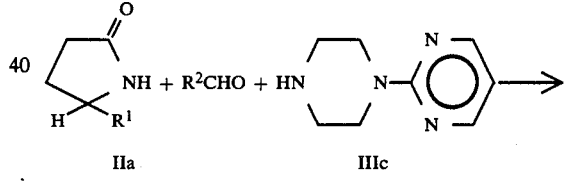

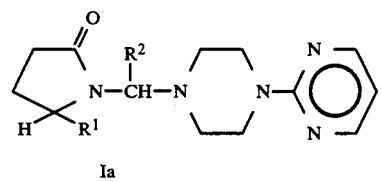

Method B:

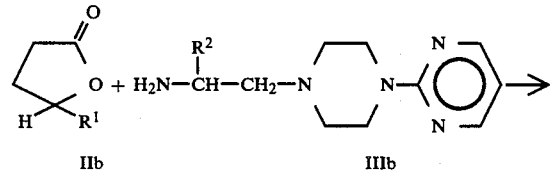

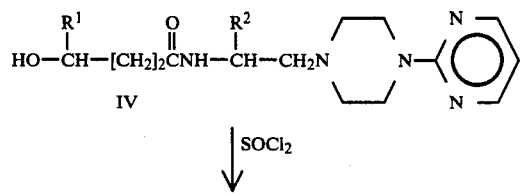

↓ SOCl$_2$

↓

-continued
Scheme 2

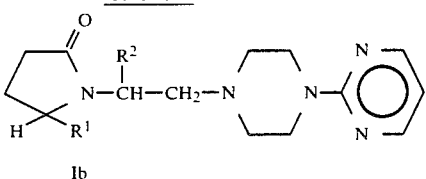

Ib

Method C:

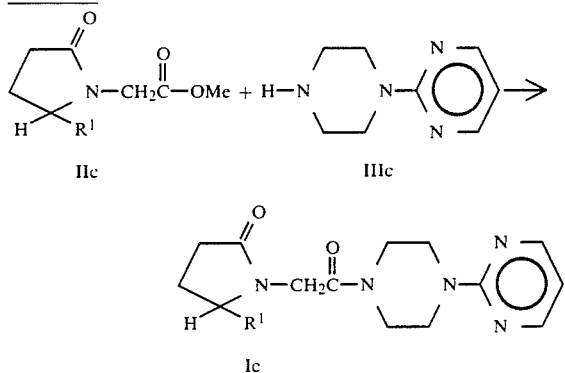

IIc + IIIb ⟶

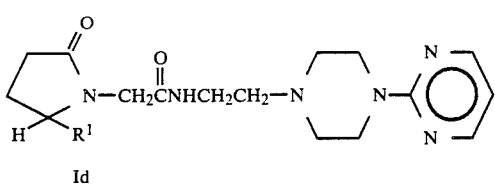

Id wherein $R^1$ and $R^2$ are as defined hereinabove.

Method A of Scheme 2 utilizes either a Mannich-type reaction of the appropriate pyrrolidinone, paraformaldehyde, and 1-pyrimidin-2-ylpiperazine or alternatively condensing an appropriate 2-pyrrolidinone, a selected aldehyde, and 1-pyrimidin-2-ylpiperazine with azeotropic removal of water. Method A will provide a product of structural Formula Ia.

In Method B, reaction of a γ-butyrolactone (IIb) with an aminoalkyl derivative of 1-pyrimidin-2-ylpiperazine (IIIb) yields an intermediate γ-hydroxyamide compound (IV) which upon treatment with thionyl chloride in an appropriate solvent, e.g. acetonitrile, undergoes cyclization to a compound of structural Formula Ib.

Method C comprises the base-catalyzed reaction of a pyrrolidinone acetate (IIc) with either 1-pyrimidin-2-ylpiperazine (IIIc) or its aminoethyl derivative (IIIb) to yield either Ic or Id.

The procedures to be used in preparing compounds of structure I by methods A–C are conventional and are readily available in the chemical literature to one skilled in the art. Examples of these methods, including synthesis of pertinent intermediates, will be exemplified later in the specification. Certain of the intermediate compounds used in the synthetic procedure discussed hereinabove are available commercially, e.g. compounds of Formula II as well as aldehydes of formula $R^2CHO$, and therefore no examples nor description of their preparation need be given.

The compounds of the instant invention are useful pharmacological agents which enhance memory and learning in mammals. In this regard, they display rat cortical EEG patterns consistent with mild CNS stimulation or patterns similar to that of a reference nootropic agent, aniracetam. Selected members of this series have been tested in a Y-maze test using aged rats and drug-induced enhancement of maze learning has been demonstrated. Additionally, other experimental procedures for determination of various CNS drug effects were carried out. The compounds of the instant series do not seem to elicit other CNS effects and thereby would seem to have an advantage as more selective agents.

The following in vivo tests were used to evaluate and classify the instant series of compounds.

TABLE 1

In Vivo Tests Used to Evaluate Formula I Compounds

1. Conditioned Avoidance Response (CAR)—measure of a drug's tranquilizing activity as determined by its attenuation of avoidance response to electrical shock in trained fasted rats. Cf: Albert, Pharmacologist, 4, 152 (1962); Wu, et al., J. Med. Chem., 12, 876–881 (1969).

2. Catelepsy Reversal—measure of a drug's ability to reverse neuroleptic-induced catelepsy in rats.

3. Vogel Anti-conflict—a test of potential anxiolytic activity which measures a drug's ability to increase licking for water in thirsty rats by subduing the animal's aversion to electrical shock.

4. EEG—a quantitive test which can serve to classify the effects of CNS compounds by comparison of their EEG profiles with those of various standard reference agents.

5. Consolidation of maze learning in aged rats—aged rats (approximately 24 months old) are food deprived 24 hours prior to training in a Y-maze. On training trials, both goal-boxes at the end of the maze are baited with food pellets. The rat may select either arm of the maze to obtain food. When an arm is chosen, the rat is detained in the chosen arm and allowed to nibble on the food reward. Rats are next immediately dosed with test compound. The critical test is 24 hours later. Rats are again food deprived overnight and placed in the maze. However, neither goal-box is baited. A correct response is scored if the rat re-enters the arm chosen the previous day. Latency for the rat to progress from start-box to goal-box is timed with a stopwatch.

6. Prevention of ECS-induced Amesia—In the training phase of this test, animals are dosed with either drug or control solutions and 30 minutes later placed on an insulated platform atop an electrified grid. When they step down from the platform, the receive an electric footshock until they scramble back to the safety of the platform. When placed upon the platform 24 hours later (a retention test), control rats do not step down; rather, they remain upon the safe platform, suggesting that they remember the aversive experience they encountered the previous day. Rats administered ECS (50 mA for 400 MSec through conrneal electrodes) immediately after training and tested 24 hours later, step down much sooner than controls. This memory deficit in ECS-treated rats reflects ECS-induced amnesia for the step-down task. Prevention of ECS-induced amnesia by test compounds is reflected in step-down latencies 24 hours after "training plus ECS" that are significantly longer than those observed in rats treated with control solutions prior to "training plus ECS."

According to the pharmacological profile established by the tests listed in Table 1, the instant compounds of Formula I have promising cognition enhancing potential in that they display EEG patterns consistent with mild CNS stimulation or they are qualitatively similar to the EEG pattern of the standard nootropic agent, aniracetam. Representative compounds selected from this series demonstrate enhanced learning in the aged rat Y-maze test and prevention of ECS-induced amnesia in normal age rats. In addition, these compounds appear to be selective agents in that low or negligible levels of activity are found in other tests indicative of different CNS effects.

The most preferred compound of the instant invention ($R^1$ and $R^2$ are hydrogen and X is a chemical bond) exhibits an EEG profile in the rat similar to that of the reference agent aniracetam, but is more potent than the latter. Enhanced potency of this compound relative to that of aniracetam has also been demonstrated in the Y-maze test employing aged rats, an appropriate behavioral model.

In summary of the foregoing discussion, the instant compounds have nootropic properties particularly suited to their use in cognition enhancement. Thus, another aspect of the instant invention concerns a process for enhancing cognition in a mammal in need of such treatment which comprises systemic administration to such mammal of an effective dose of a Formula I compound or a pharmaceutically acceptable acid addition salt thereof. The administration and dosage regimen of compounds of Formula I is considered to be done in the same manner as for the reference compound piracetam, cf: Reisberg, et al., in *Drug Development Research*, 2:475-480 (1982); Weng, et al., in *Rational Drug Therapy*, 17(5), 1-4 (1983); Reisberg, et al., in "Psychopathology in the Aged, Editors, Cole and Barrett, Raven Press, New York, pages 243-245 (1980). Although the dosage and dosage regimen must in each case be carefully adjusted, utilizing sound professional judgment and considering the age, weight and condition of the recipient, the route of administration and the nature and extent of mental deterioration, generally, the daily dosage will be from about 0.1 g to about 10 g, preferably 0.5 g to 5 g, when given orally. In some instances, a sufficient therapeutic effect can be obtained at lower doses while in others, larger doses will be required. As is apparent to one skilled in clinical pharmacology the amount of Formula I compound comprising the daily dose may be given in a single or divided dose, taking into account those principles understood by the skilled practitioner and necessary for his practice of the art.

The term systemic administration as used herein refers to oral, rectal, and parenteral (i.e., intramuscular, intravenous and subcutaneous) routes. Generally, it will be found that when a compound of the present invention is administered orally which is the preferred route, a larger quantity of the active drug is required to produce the same effect as the smaller quantity given parenterally. In accordance with good clinical practice, it is preferred to administer the instant compounds at a concentration level that will produce effective nootropic effects without causing any harmful or untoward side effects.

Therapeutically, the instant compounds are generally given as pharmaceutical compositions comprised of an effective nootropic amount of a compound of Formula I or a pharmaceutically acceptable acid addition salt thereof and a pharmaceutically acceptable carrier. Pharmaceutical compositions for effecting such treatment will contain a major or minor amount (e.g. from 95 to 0.5%) of at least one compound of the present invention in combination with a pharmaceutical carrier, the carrier comprising one or more solid, semi-solid, or liquid diluent, filler and formulation adjuvant which is non-toxic, inert and pharmaceutically acceptable. Such pharmaceutical compositions are preferably in dosage unit forms; i.e., physically discrete units having a pre-determined amount of the drug corresponding to a fraction or multiple of the dose which is calculated to produce the desired therapeutic response. The dosage units can contain 1, 2, 3 or more single doses, or alternatively, one-half, one-third, or less of a single dose. A single dose preferably contains an amount sufficient to produce the desired therapeutic effect upon administration at one application of one or more dosage units according to the pre-determined dosage regimen, usually a whole, half, third or quarter of the daily dosage administered once, twice, three, or four times a day. It is envisioned that other therapeutic agents can also be present in such a composition. Pharmaceutical compositions which provide from about 0.1 to 1 g of the active ingredient per unit dose are preferred and are conveniently prepared as tablets, lozenges, capsules, powders, aqueous or oily suspensions, syrups, elixirs, and aqueous solutions. Preferred oral compositions are in the form of tablets, capsules, and may contain conventional excipients such as binding agents (e.g., syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethyleneglycol or silica), disintegrants (e.g. starch) and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection. Such compositions having the desired clarity, stability and adaptability for parental use are obtained by dissolving from 0.1% to 10% by weight of the active compound in water or a vehicle consisting of a polyhydric aliphatic alcohol such as glycerine, propylene glycol, and the polyethylene glycols or mixtures thereof. The polyethylene glycols consist of a mixture of non-volatile, usually liquid, polyethylene glycols which are soluble in both water and organic liquids and which have molecular weights from about 200 to 1500.

DESCRIPTION OF SPECIFIC EMBODIMENTS

The compounds which constitutes this invention and their methods of preparation will appear more fully from a consideration of the following examples which are given for the purpose of illustration only and are not to be construed as limiting the invention in sphere or scope. All temperatures are understood to be in degrees C. when not specified.

The nuclear magnetic responance (NMR) spectral characteristics refer to chemical shifts ($\delta$) expressed as parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), singlet (s), multiplet (m), doublet (d), doublet of doublets (dd), or quartet (q). Abbreviations employed are DMSO-d$_6$ (deuterodimethylsulfoxide), CDCl$_3$ (deuterochloroform), and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight.

Synthesis of Intermediates

EXAMPLE 1

1-(Pyrimidin-2-yl)piperazine (IIIc)

To a stirred, warm (approximately 50°) solution of anhydrous piperazine (100 g, 1.16 mole) and sodium carbonate (58 g, 0.47 mole) in 465 mL water was added 2-chloropyrimidine (53 g, 0.46 mole) in portions over about 1 hour. External cooling was required to maintain the temperature in the 50°-65° range. After the addition, the stirred reaction mixture was kept in the temperature range of 50°-65° for one hour and then allowed to slowly cool to 35° over a 2 hour period. The mixture was filtered, removing 1,4-dipyrimidinylpiperazine, and the filtrate was extracted with 350 mL portions of chloroform. The chloroform extracts were dried (MgSO$_4$) and concentrated to 62 g (82%) of an oily solid which can be purified by distillation (b.p. 118°-120°/2 Torr.) or converted to a salt form.

EXAMPLE 2

2-[4-(2-Pyrimidinyl)-1-piperazinyl] ethanamine (IIIb)

A mixture of N-(2-bromoethyl)phthalimide (38.1 g, 0.15 mole), 1-(pyrimidin-2-yl)piperidine (24.6 g, 0.15 mole; prepared in Example 1), pulverized K$_2$CO$_3$ (20.7 g, 0.15 mole) and KI (1.5 g) in 450 mL acetonitrile was magnetically stirred and heated under reflux for 16 hr. The hot reaction mixture was filtered and the filtrate refrigerated. The crystalline precipite which formed was collected by filtration to give 21.4 g white solid. A second crop which was obtained by partial concentration of the filtrate was recrystallized from isopropyl alcohol and combined with the initial crop for a total yield of 26.1 g (51%) of phthalimide intermediate, m.p. 119°-122°. The latter intermediate (26.1 g, 0.077 mole) and 5.9 mL 99% hydrazine hydrate in 210 mL ethanol was stirred and heated under reflux for 16 hr. The cooled reaction mixture was filtered and concentrated in vacuo to a solid residue which was triturated with 20 mL water and 75 mL chloroform. The aqueous phase was made strongly alkaline with 50% NaOH solution, the organic phase separated and the aqueous phase extracted with several portions of chloroform. The combined chloroform fractions were dried (MgSO$_4$) and concentrated in vacuo to a yellow oil which was purified by Kugelrohr distillation at 0.2 Torr. to afford 7.9 g (50%) of product.

Synthesis of I Products

EXAMPLE 3

1-[[4-(2-Pyrimidinyl)-1-piperazinyl]methyl]-2-pyrrolidinone (Method A)

A mixture of 2-pyrrolidinone (13.6 g, 0.6 mole), 1-(pyrimidin-2-yl)piperazine (26.2 g, 0.16 mole) and paraformaldehyde (19.6 g, 0.65 mole) and 420 mL ethanol was stirred and heated under reflux for 16 hour period. The hot solution was filtered and refrigerated and the crystalline precipitate which formed was collected by filtration and recrystallized twice from ethanol to give 19.5 g (47%) of white solid, m.p. 161°-163°.

Anal. Calcd. for C$_{13}$H$_{19}$N$_5$O: C, 59.75; H, 7.33; N, 26.80. Found: C, 59.73; H, 7.38; N, 26.88.

NMR (CDCl$_3$): 2.00 (2, m); 2.39 (2, t [7.0 Hz]); 2.57 (4, m); 3.49 (2, t [6.8 Hz]); 3.81 (4, m); 4.02 (2, s); 6.43 (1, t [4.8 Hz]); 8.27 (2, d [4.8 Hz]).

IR (KBr): 795, 980, 1000, 1280, 1365, 1515, 1545, 1585, 1675, 2780, 2800, 2910, and 2950 cm$^{-1}$.

5-Methyl-1-[[4-(2-pyrimidinyl)-1-piperazinyl]methyl]-2-pyrrolidinone Hydrochloride This compound can be prepared in a similar fashion by use of the procedure outlined in Example 3. The crude base product was an oil, b.p. 190°-200°/0.1 Torr, which was converted to the HCl salt by treatment with ethanolic HCl. Recrystallization of the HCl salt from ethanol gives a 68% yield of white solid, m.p. 188°-190°.

Anal. Calcd. for C$_{14}$H$_{21}$N$_5$O.HCl: E, 53.93; H, 7.11; N, 22.46. Found: C, 53.64; H, 7.04; N, 22.49.

EXAMPLE 5

1-[(2-Chlorophenyl)[4-(2-pyrimidinyl)-1-piperazinyl]methyl]-2-pyrrolidinone

A solution of 2-pyrrolidinone (4.25 g, 0.05 mole), 1-(pyrimidin-2-yl)piperazine (8.2 g, 0.05 mole) and 2-chlorobenzaldehyde (7.05 g, 0.05 mole) in 200 mL toluene was stirred and heated for 16 hour with an attached Dean-Stark trap for azeotropic removal of water. The solution was concentrated in vacuo to provide 16.2 g, (87%) of product. Recrystallization from ethanol gave white crystals, m.p. 166°-177°.

Anal. Calcd. for C$_{19}$H$_{22}$ClN$_5$O: C, 61.37; H, 5.96; N, 18.83; Cl, 9.53. Found: C, 61.00; H, 6.15; N, 18.75; Cl, 9.32.

NMR (CDCl$_3$): 1.92 (2, m); 2.42 (2, m); 2.55 (4, m); 2.86 (1, m); 3.31 (1, m); 3.85 (4, m); 5.84 (1, s); 6.47 (1, t [4.7 Hz]); 7.32 (3, m); 7.80 (1, m); 8.27 (2, ds [4.7 Hz]).

IR (KBr): 770, 795, 980, 1260, 1360, 1450, 1500, 1545, 1585, 1690 cm$^{-1}$.

EXAMPLE 6

1-[(3-Chlorophenyl)[4-(2-pyrimidinyl)-1-piperazinyl]methyl]-2-pyrrolidinone

Employing 3-chlorobenzaldehyde, this compound was prepared in a similar manner following the procedure outlined in Example 5. Recrystallization from cyclo-hexane gave a 62% yield of white powder, m.p. 136-138.5.

Anal. Calcd. for C$_{19}$H$_{22}$ClN$_5$O: C, 61.34; H, 5.96; N, 18.83; Cl, 9.53. Found: C, 61.14; H, 6.03; N, 18.75; Cl, 9.66.

EXAMPLE 7

1-[(4-Methoxyphenyl)[4-(2-pyrimidinyl)-1-piperazinyl]methyl]-2-pyrrolidinone

Employing 4-methoxybenzaldehyde, this product was similarly prepared utilizing the basic procedure outlined in Example 5. Recrystallization of the product from cyclohexane gave an 81% yield of white crystals, m.p. 166.5°-169.5°.

Anal. Calcd. for C$_{20}$H$_{25}$N$_5$O$_2$: C, 65.38; H, 6.86; N, 19.06. Found: C, 65.33; H, 6.97; N, 19.14.

EXAMPLE 8

1-[(4-Cyanophenyl)[4-(2-pyrimidinyl)-1-piperazinyl]methyl]-2-pyrrolidinone

Employing 4-cyanobenzaldehyde, this product was prepared as in Example 5. Chromatography on silica gel eluting with ethyl acetate gave a 16% yield of product, m.p. 185°-188°.

Anal. Calcd. for $C_{20}H_{22}N_6O$: C, 66.28; H, 6.12; N, 23.19. Found: C, 66.55; H, 6.40; N, 22.59.

EXAMPLE 9

1-[2-[4-(2-Pyrimidinyl)-1-piperazinyl]ethyl]-2-pyrrolidinone hydrochloride hydrate (Method B)

A solution of γ-butyrolactone (1.81 g, 0.02 mole), 2-[4-(2-pyrimidinyl)-1-piperazinyl]ethanamine (4.52 g, 0.02 mole: prepared in Example 2), and a catalytic amount of p-toluene-sulfonic acid in 28 mL benzene was stirred and heated at reflux for 6 hours. The precipitate which crystallized upon standing at room temperature was collected by filtration and air dried to afford 3.78 g (61%) of the γ-hydroxyamide intermediate (IV), m.p. 93°-97°. A mixture of IV (3.6 g, 0.012 mole) and thionyl chloride (1.45 g, 0.012 mole) in 30 mL acetonitrile was stirred and heated at reflux for 16 hour. A crystalline precipitate which resulted after cooling to room temperature and was collected and recrystallized from isopropyl alcohol to give 2.66 g (69%) of white solid, m.p. 185°-187°.

Anal. Calcd. for $C_{14}H_{21}N_5O.2.2HCl.0.2H_2O$: C, 46.05; H, 6.60; N, 19.60; Cl, 21.83; $H_2O$, 0.50. Found: C, 46.90; H, 6.68; N, 20.09; Cl, 21.83; $H_2O$, 0.48.

NMR (DMSO-$d_6$): 1.96 (2, m); 2.30 (2, m); 3.20 (4, m); 3.55 (6, m); 3.64 (2, t [6.7 Hz]); 4.58 (2, m); 5.40 (1, bs); 6.75 (1, t [4.9 Hz]); 8.49 (2, d [4.9 Hz]); 11.50 (1, bs).

IR (KBr): 795, 950, 980, 1370, 1435, 1475, 1555, 1590, 1665 cm$^{-1}$.

EXAMPLE 10

1-[(2-Oxo-1-pyrrolidinyl)acetate]-4-(2-pyrimidinyl)piperazine-2-propanolate (Method C)

A solution of methyl 2-oxo-1-pyrrolidineacetate (12.58 g, 0.08 mole), 1-(pyrimidinyl-2-yl)piperazine (13.12 g, 0.08 mole) and sodium (1.84 g, 0.08 mole) in 200 mL methanol was stirred and heated under reflux for 16 hour. The cooled reaction mixture was diluted with saturated sodium chloride solution and extracted with methylene chloride. The dried (MgSO$_4$) extract was concentrated in vacuo and the residual solid recrystallized twice from isopropanol to afford 7.66 g (32%) of white solid, m.p. 185°-187°.

Anal. Calcd. for $C_{14}H_{19}N_5O_2.0.1C_3H_8O$: C, 58.15; H, 6.76; N, 23.71. Found: C, 57.76; H, 6.80; N, 23.55.

NMR (CDCl$_3$): 2.06 (2, m); 2.42 (2, m); 3.61 (6, m); 3.78 (4, m); 4.19 (2, s); 6.50 (1, t [4.8 Hz]); 8.28 (1, d [4.8 Hz]).

IR (KBr): 795, 980, 1240, 1260, 1305, 1355, 1490, 1545, 1580, 1645, 1680, 2860, 2930, 3020 cm$^{-1}$.

EXAMPLE 11

2-Oxo-N-[2-[4-(2-pyrimidinyl)-1-piperazinyl]ethyl]-1-pyrrolidineacetamide hydrate This compound was prepared using a procedure similar to that outlined in Example 10. Recrystallization from isopropyl alcohol gave a 40% yield of an off-white solid, m.p. 105°-107.5°.

Anal. Calcd. for $C_{16}H_{24}N_6O_2.0.2H_2O$: C, 57.19; H, 7.32; N, 25.01; $H_2O$, 1.07. Found: C, 56.98; H, 7.25; N, 24.71; $H_2O$, 0.39.

Further Detailed Description of the Invention

Some additional compounds which are related to those defined hereinabove by Formula I have been made and tested and found to have useful psychopharmacological properties. These compounds, as well as the other compounds of Formula I, supra., have been found to be useful when employed as cognition enhancing agents or mild stimulants of the central nervous system. In addition, these compounds have been found to be useful in preventing amnesia which results from electroconvulsive shock. Such activity not only relates to memory retention in normal aging and senility processes but would be useful in protecting against the amnesia-producing effects of electroconvulsant shock as used clinically. Electroconvulsant shock is employed to treat some classes of psychiatric patients, particularly depressed patients refractory to traditional pharmaco therapy. It is well documented that these electroconvulsant shock treatments induce the undesirable side-effect of amnesia in those patients to whom it is administered. The instant compounds which exhibit activity in protecting against the amnesia-producing effects of electroconvulsant shock in pharmacological testing would be useful adjuncts to the clinical use of electroconvulsant shock in psychiatric treatment.

These additional compounds are new products related to Formula I, supra., and are embodied as Formula I'.

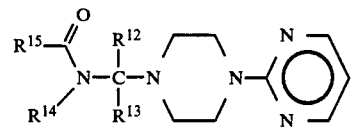

For compounds of Formula I'; $R^{12}$ is hydrogen, pyridinyl or 1-methylpyrrolyl; and $R^{13}$ is hydrogen. $R^{14}$ can be hydrogen or $C_{1-4}$ alkyl; $R^{15}$ can be $C_{1-4}$ alkyl; or $R^{14}$ and $R^{15}$ may be combined to give: substructure (a)

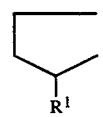

wherein $R^1$ is hydrogen or $C_{1-4}$ alkyl; substructure (b)

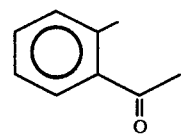

or substructure (c)

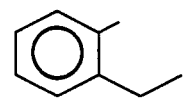

Additionally, $R^{13}$ and $R^{15}$ can be combined as substructure (d) when $R^{14}$ is hydrogen.

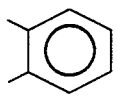 (d)

Some representative compounds of Formula I' are exemplified below in Table 1.

TABLE 1

Formula I' Compounds $$R^{15}\overset{O}{\underset{R^{14}}{\underset{|}{N}}}-\overset{R^{12}}{\underset{R^{13}}{\underset{|}{C}}}-N\underset{\diagdown}{\diagup}N-\overset{N}{\underset{N}{\diagdown}}$$ I'

| Ex. | $R^{12}$ | $R^{13}$ | $R^{14}$ | $R^{15}$ | m.p. (°C.) | Mol. Formula |
|---|---|---|---|---|---|---|
| 12 | (pyridinyl) | H | (a; with $R^1$=H) | | 221–226 dec. | $C_{18}H_{22}N_6O$ |
| 13 | (N-methylpyrrolyl) | H | (a; with $R^1$=H) | | 165–169 dec. | $C_{18}H_{24}N_6O$ |
| 14 | H | H | (b) | | 199–201.5 | $C_{17}H_{17}N_5O_2$ |
| 15 | H | H | (c) | | 154–156.5 | $C_{17}H_{19}N_5O$ |
| 16 | H | H | $CH_3$ | $CH_3$ | 117–123 | $C_{12}H_{19}N_5O$ |
| 17 | H | (d) | H | (d) | 251–253 dec. | $C_{16}H_{17}N_5O \cdot 0.15\ C_3H_8O$ |

*The C, H, and N elemental analyses were within ±0.4% of theory for molecular formula displayed.

The compounds of Formula I' are generally prepared using method A, or an appropriate modification, as shown in Scheme 2, supra. For preparation of the compounds of Formula I' by means of method A, a Mannich-type reaction using an appropriate amide or imide with either an aromatic or heteroaromatic aldehyde or paraformaldehyde and 1-(2-pyrimidinyl)piperazine. Formula I' compounds having substructure (d) such as Example 17, are readily made by heating 3-hydroxyisoindolone with 1-(2-pyrimidinyl)piperazine in toluene with the aeotropic removal of water.

EXAMPLE 17

2,3-Dihydro-3-[4-(2-pyrimidinyl)-1-piperazinyl]-1H-isoindol-1-one 2-Propanoate

A mixture of 3-hydroxyisoindolone (2.98 g, 0.02 mole) and 1-(2-pyrimidinyl)piperazine (3.28 g, 0.02 mole) was refluxed in toluene (75 mL) under a Dean-Stark trap for 22 hour. The toluene was then removed in vacuo and the crude product was recrystallized three times from isopropanol to give 3.13 g (53%) of a white powder (m.p. 152.5°–156°.

EXAMPLE 18

Reversal of ECS-Induced Amnesia For Step-Down Passive Avoidance Response

In the step-down passive advoidance procedure, rats are trained to remain immobile to avoid foot shock. Two control groups (n=36/group) were required; an ECS control and a sham-ECS control. ECS control animals were placed individually on a platform over an activated shock grid (0.8 mA) 30 minutes after vehicle administration. The animals readily stepped down from the platform, immediately experienced the foot shock, and quickly learned to escape to the platform. An animal was considered to have acquired the passive avoidance response if it remained on the platform for two minutes without stepping down following foot shock delivery. Immediately after acquisition, the ECS control animals were delivered ECS via transcorneal electrodes at an intensity of 50 mA for 400 milliseconds. The sham-ECS control animals were treated in a manner identical to that described for the ECS controls, with the exception that the current was not passed through the transcorneal electrodes. Both groups were administered a retention test 24 hours later. Animals were placed individually on the platform, and the latency to step down from the platform onto the unactivated shock grid was recorded; a given subject animal was considered to have retained the passive avoidance response if it remained on the platform for 300 seconds without stepping down. Sham-ECS controls remained on the platform during this test, showing normal retention; ECS controls readily stepped down within 300 seconds, exhibiting a deficit in retention (i.e., amnesia).

Step-down latency scores were transformed into percent retention scores with 300 seconds equal 100% retention. The percent retention scores for all drug groups were evaluated against both the ECS and sham-ECS control groups using Dunnett's test. A compound was considered to be active in this test if the mean retention score obtained from at least one dose group is both significantly greater than the ECS control group retention and not significantly different from the sham-ECS control group retention. This indicates that the test compounds reversed the amnesia for the passive avoidance task induced by the ECS. The compounds which statistically raised the animals' performance above that of the ECS control group, but did not raise the performance sufficiently to be not statistically different from the sham-ECS control group were scored as possessing "intermediate activity". These compounds, then, do statistically raise the animals' performance, but not sufficiently to give total protection against the amnesia.

Biological test data of selected Formula I' compounds resulting from the test outlined in Example 18 are given in Table 2.

TABLE 2

Biological Activities of Formula I' Compounds in Reversal of ECS-Induced Amnesia

| Example | ECS-Induced Amnesia Reversal* |
|---|---|
| 12 | active at 1 mg/kg s.c. |
| 13 | intermediate activity at 1 mg/kg s.c. |
| 14 | active at 1 mg/kg s.c. |
| 15 | active at 25 mg/kg s.c. |
| 16 | intermediate activity at 25 mg/kg s.c. |

TABLE 2-continued
Biological Activities of Formula I'
Compounds in Reversal of ECS-Induced Amnesia

| Example | ECS-Induced Amnesia Reversal* |
|---------|-------------------------------|
| 17      | active at 25 mg/kg s.c.       |

*"active" denotes compounds which completely reversed the ECS-induced amnesia while "intermediate activity" denotes less than complete protection as described in Example 18.

The scope of the instant invention is hereby expanded to include the compounds defined by Formula I' as well as those heretofore embraced by Formula I. The present subject matter can now be defined by Formula XXI (shown below) which is comprised of the compounds Formula I and I'

XXI and pharmaceutically acceptable acid addition salts thereof. In Formula XXI, $R^2$ can be hydrogen, lower alkyl, phenyl, optimally substituted at one or two ring positions with lower alkyl, halogen, trifluoromethyl, cyano, nitro, formyl, carbonyl-lower-alkyl, alkylamino, dialkylamino, carbonyl-lower-alkyloxy, carbonylphenoxy, carbonylphenalkyloxy, lower-alkyloxy, phenoxy, or phenyl-lower-alkyloxy; pyridinyl or 1-methylpyrrolyl. $R^7$ is hydrogen or it can be combined with $R^9$ as explained below. $R^8$ can be hydrogen or lower alkyl and $R^9$ can be lower alkyl; or $R^8$ and $R^9$ may be combined to give the following structural variants: substructure (a)

(a)

wherein $R^1$ is hydrogen or lower alkyl substructure (b)

(b)

substructure (c)

(c)

Additionally, $R^7$ and $R^9$ can be combined as substructure (d)

(d)

when $R^8$ is hydrogen. X can be a chemical bond, $$-\overset{O}{\underset{\|}{C}}-,\ -CH_2-,\ \text{or}\ -\overset{O}{\underset{\|}{C}}NHCH_2CH_2-.$$

What is claimed is:
1. A compound of Formula XXI

XXI and the pharmaceutically acceptable acid addition salts thereof wherein $R^2$ is hydrogen, lower(meaning from 1 to 4 atoms) alkyl, pyridinyl, 1-methylpyrrolyl, or phenyl, optimally substituted at one or two ring positions with lower alkyl, halogen, hydrogen, trifluoromethyl, cyano, nitro, formyl, carbonyl-lower-alkyl, lower-alkylamino, di-lower-alkylamino, carbonyl-lower-alkyloxy, carbonylphenoxy, carbonylphenyl-lower-alkyloxy, lower-alkyloxy, phenoxy, or phenyl-loweralkyloxy;

$R^7$ is hydrogen;
$R^8$ is hydrogen or lower alkyl; and
$R^9$ is lower alkyl; or
$R^8$ and $R^9$ are combined to give:
substructure (a)

(a)

wherein $R^1$ is hydrogen or lower alkyl, substructure (b);

(b)

substructure (c); and (c)

$R^7$ and $R^9$ are combined as substructure (d)

(d)

when $R^8$ is hydrogen; and
X is a chemical bond,

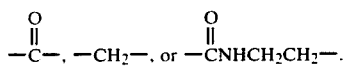

2. A compound of claim 1 wherein $R^8$ and $R^9$ are combined to give substructure (a)

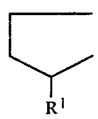

3. The compound of claim 1 wherein $R^2$ is hydrogen.
4. The compound of claim 1 wherein X is a chemical bond.
5. The compound of claim 1 wherein $R^8$ and $R^9$ are combined to give substructure (b)

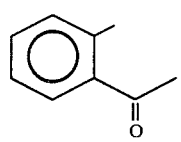

6. The compound of claim 1 wherein $R^2$ is pyridinyl.
7. The compound of claim 1, 1-[[4-2-pyrimidinyl)-1-piperazinyl]methyl]-2-pyrrolidinone.
8. The compound of claim 1, 5-methyl-1-[[4-(2-pyrimidinyl)-1-piperazinyl]methyl]-2-pyrrolidinone.
9. The compound of claim 1, 1-[(2-chlorophenyl)-[4-(2-pyrimidinyl)-1-piperazinyl]methyl]-2-pyrrolidinone.
10. The compound of claim 1, 1-[(3-chlorophenyl)-[4-(2-pyrimidinyl)-1-piperazinyl]methyl]-2-pyrrolidinone.

11. The compound of claim 1, 1-[(4-methoxyphenyl)[4-(2-pyrimidinyl)-1-piperazinyl]methyl]-2-pyrrolidinone.
12. The compound of claim 1, 1-[(4-cyanophenyl)-[4-(2-pyrimidinyl)-1-piperazinyl]methyl]-2-pyrrolidinone.
13. The compound of claim 1, 1-[2-[4-(2-pyrimidinyl)-1-piperazinyl]ethyl]-2-pyrrolidinone.
14. The compound of claim 1, 1-[(2-oxo-1-pyrrolidinyl)acetyl]-4-(2-pyrimidinylpiperazine-[2-propanolate].
15. The compound of claim 1, 2-oxo-N-[2-[4-(2-pyrimidinyl)-1-piperazinyl]ethyl]-1-pyrrolidineacetamide.
16. The compound of claim 1, 1-[(4-pyridinyl)-[4-(2-pyrimidinyl)-1-piperazinyl]methyl]-2-pyrrolidinone.
17. The compound of claim 1, 1-[(1-methyl-1H-pyrrol-2-yl([4-(2-pyrimidinyl)-1-piperazinyl]methyl]-2-pyrrolidinone.
18. The compound of claim 1, 2-[[4-(2-pyrimidinyl)-1-piperazinyl]methyl]-1H-isoindole-1,3-(2H)-dione.
19. The compound of claim 1, 2,3-dihydro-2-[[4-(2-pyrimidinyl)-1-piperazinyl]methyl]-1H-isoindol-1-one.
20. The compound of claim 1, N-methyl-N-[[4-(2-pyrimidinyl)-1-piperazinyl]methyl]acetamide.
21. The compound of claim 1, 2,3-dihydro-3-[4-(2-pyrimidinyl)-1-piperazinyl]-1H-isoindol-1-one.
22. The method for enhancing cognition in a mammal in need of such treatment which comprises systemic administration to the mammal of an effective dose of a compound claimed in claim 1.
23. The method for enhancing memory in a mammal in need of such treatment which comprises systemic administration to the mammal of an effective dose of a compound claimed in claim 1.
24. A pharmaceutical composition in dosage unit form suitable for systemic administration to a mammalian host comprising a pharmaceutical carrier and from about 0.5 to 1 g of a compound claimed in claim 1.

* * * * *